United States Patent
Wang et al.

(10) Patent No.: US 9,693,573 B2
(45) Date of Patent: Jul. 4, 2017

(54) REAL-TIME REMOTE DATA COLLECTING SYSTEMS AND METHODS

(71) Applicant: Nestec SA, Vevey (CH)

(72) Inventors: Xue Ling Wang, Beijing (CN); David Chih-Hung Chang, Gurgaon (IN); Bao Zhong Hu, Shanghai (CN); Ruguo Hu, Shanghai (CN)

(73) Assignee: NESTEC SA, Vevey (CH)

( * ) Notice: Subject to any disclaimer, the term of this patent is extended or adjusted under 35 U.S.C. 154(b) by 624 days.

(21) Appl. No.: 13/785,896

(22) Filed: Mar. 5, 2013

(65) Prior Publication Data

US 2014/0257753 A1    Sep. 11, 2014

Related U.S. Application Data

(60) Provisional application No. 61/607,089, filed on Mar. 6, 2012.

(51) Int. Cl.
| | | |
|---|---|---|
| G06F 11/00 | (2006.01) | |
| A23K 1/00 | (2006.01) | |
| A23K 50/40 | (2016.01) | |

(52) U.S. Cl.
CPC ............... *A23K 1/00* (2013.01); *A23K 50/40* (2016.05)

(58) Field of Classification Search
CPC .............................. A01K 5/0114; H04L 67/12
See application file for complete search history.

(56) References Cited

U.S. PATENT DOCUMENTS

| | | | |
|---|---|---|---|
| 5,706,980 A | 1/1998 | Dickerson | |
| 5,801,715 A | 9/1998 | Norman | |
| 8,925,485 B2 * | 1/2015 | Pu ........................ | A01K 5/0114 |
| | | | 119/51.02 |
| 2004/0194714 A1* | 10/2004 | Lee ....................... | A01K 5/0114 |
| | | | 119/54 |
| 2007/0125306 A1 | 6/2007 | Beecher | |
| 2007/0181068 A1 | 8/2007 | McKeown | |
| 2008/0252464 A1 | 10/2008 | Panasevich | |
| 2010/0073666 A1 | 3/2010 | Perkins et al. | |
| 2010/0240962 A1 | 9/2010 | Contant | |
| 2010/0263596 A1* | 10/2010 | Schumann ........... | A01K 5/0114 |
| | | | 119/51.02 |

(Continued)

FOREIGN PATENT DOCUMENTS

| | | |
|---|---|---|
| JP | H06332782 A | 12/1994 |
| JP | 2002120904 | 4/2002 |

(Continued)

OTHER PUBLICATIONS

International Search Report and Written Opinion for PCT/US2013/029139, dated May 3, 2013.
EP Extended Search Report for EP13757169 Dated Feb. 23, 2015.

*Primary Examiner* — Elias Desta

(57) ABSTRACT

The invention relates generally to remote data collecting systems and methods. In a general aspect, the present invention provides a remote data collecting system comprising a measuring device having at least two scales in communication with a web server. The web server can be used to display data from the measuring device on a website to be accessed by one or more users, for example, using a computing device. The remote data collecting system is particularly useful for real-time, uncontrolled environment (e.g., in-home) product testing.

20 Claims, 6 Drawing Sheets

(56) References Cited

U.S. PATENT DOCUMENTS

2010/0299074 A1* 11/2010 Chang .................. A01K 5/00
   702/19
2010/0319627 A1   12/2010 Cauchy et al.

FOREIGN PATENT DOCUMENTS

| JP | 2005060225    | 3/2005 |
| JP | 2005253850    | 9/2005 |
| JP | 2005253850 A2 | 9/2005 |
| JP | 2010090040    | 4/2010 |
| JP | 2011502258 A  | 1/2011 |
| JP | 2012521584    | 9/2012 |
| WO | 03013232 A1   | 2/2003 |
| WO | 2009056260    | 5/2009 |

* cited by examiner

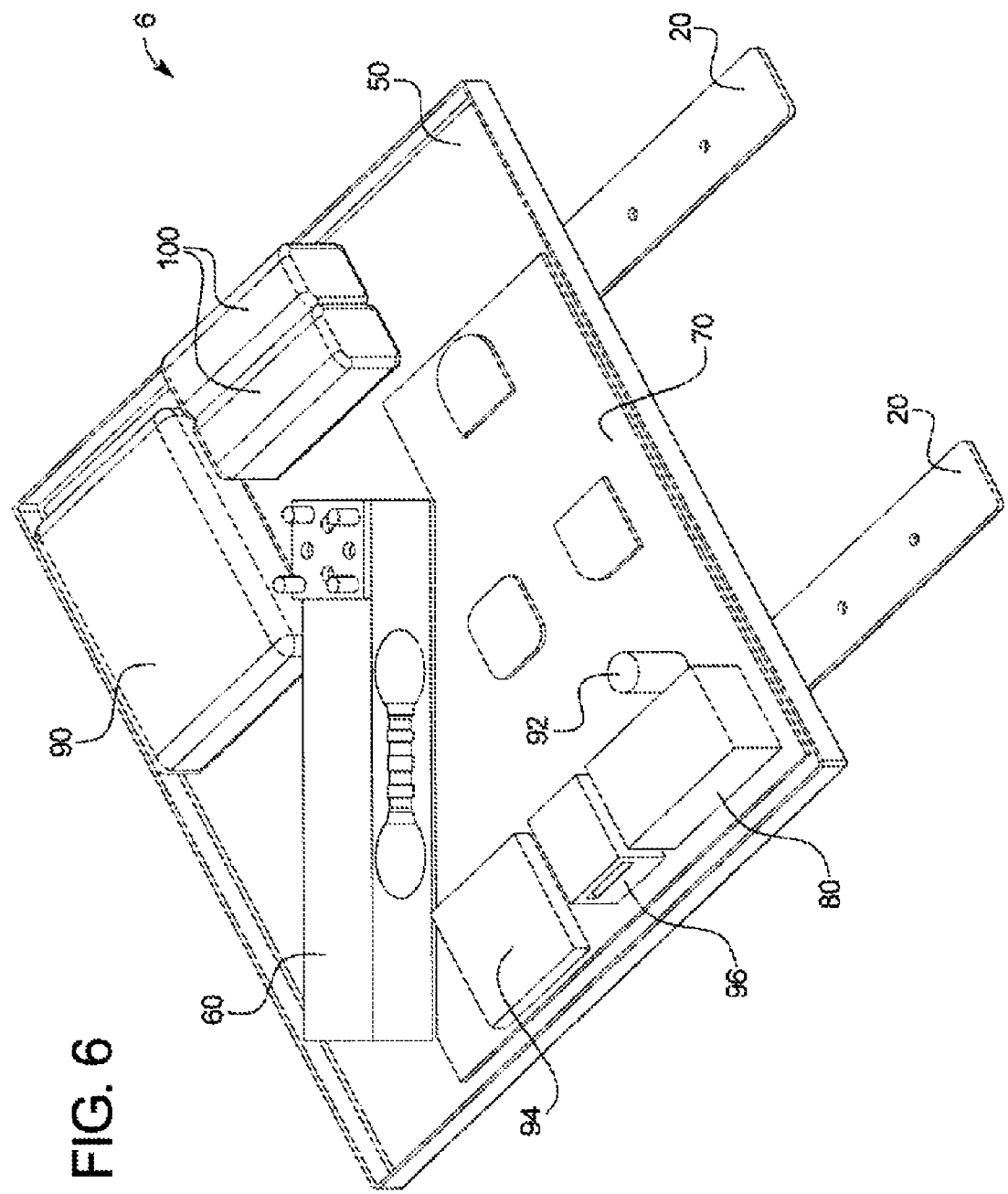

REAL-TIME REMOTE DATA COLLECTING SYSTEMS AND METHODS

CROSS REFERENCE TO RELATED APPLICATIONS

This application claims priority to U.S. Provisional Application Ser. No. 61/607,089 filed 6 Mar. 2012, the disclosure of which is incorporated herein by this reference.

BACKGROUND OF THE INVENTION

Field of the Invention

The invention relates generally to remote data collecting systems and methods and particularly to real-time remote data collecting systems and methods.

Description of Related Art

Product testing generally takes place in a controlled environment such as a laboratory or research facility. Products such as human or pet foods can be conveniently tested at these locations because of the instruments and tools available to determine related parameters such as product nutritional quality, product physical characteristics, animal consumption rates, and consumption times. Similarly, the palatability of human or pet foods is generally tested in controlled environments. However, testing products such as foods for palatability or other parameters in a controlled environment such as a laboratory or research facility has limitations. The tests may not accurately reproduce the actual environment where the foods will be consumed. For example, a test subject's actual surroundings may affect their perceptions and taste preferences. Similarly, controlled environments such as a laboratory may not be available for needed testing. Circumstances may require that such tests be conducted in multiple locations that are inconvenient for those conducting the tests, e.g., in-home palatability tests for pet foods. Therefore, there is a need for remote data collecting systems that collect and analyze data from uncontrolled environments and can be accessed by one or more users in real-time, including systems for collecting data from one or more in-home environments or environments that are situated at a long distance.

SUMMARY OF THE INVENTION

It is, therefore, an object of the invention to provide improved remote data collecting systems and methods.

It is another object of the invention to provide a method of collecting data remotely.

It is yet another object of the invention to provide a method of testing the palatability of pet food remotely and in real-time.

It is still another object of the invention to provide a method of testing the palatability of pet food in real-time in a domestic environment.

It is still another object of the invention to provide kits having devices and instructions for remote data collecting systems and methods.

It is another object of the invention to provide packages and indicia describing the contents of the package including remote data collecting systems and methods.

These and other objects are achieved using a remote data collecting system comprising a measuring device having at least two scales in communication with a web server and a computing device in communication with the web server that hosts a web site having information/database regarding the measuring device. Each of the scales can include a product. Testing the palatability and/or other consumption related data for pet food can be done in a domestic or in-home environment. In addition, with internet accessibility, it becomes advantageously possible that anyone who can access the web site can view the database and operate the system.

Additional features and advantages of the invention will be readily apparent to those skilled in the art.

BRIEF DESCRIPTION OF THE DRAWINGS

FIG. 6 illustrates the internal components of the scale of the remote data collecting system in an embodiment of the invention.

DETAILED DESCRIPTION OF THE INVENTION

Definitions

Figure 1:
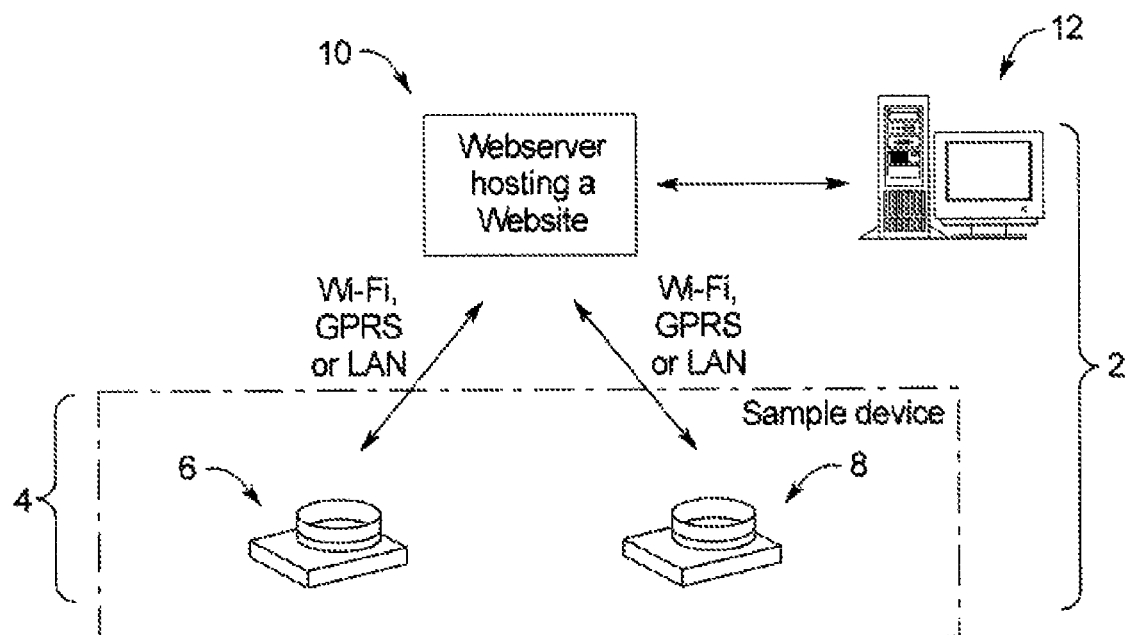
FIG. 1 illustrates the remote data collecting system in an embodiment of the invention.
Figure 2:
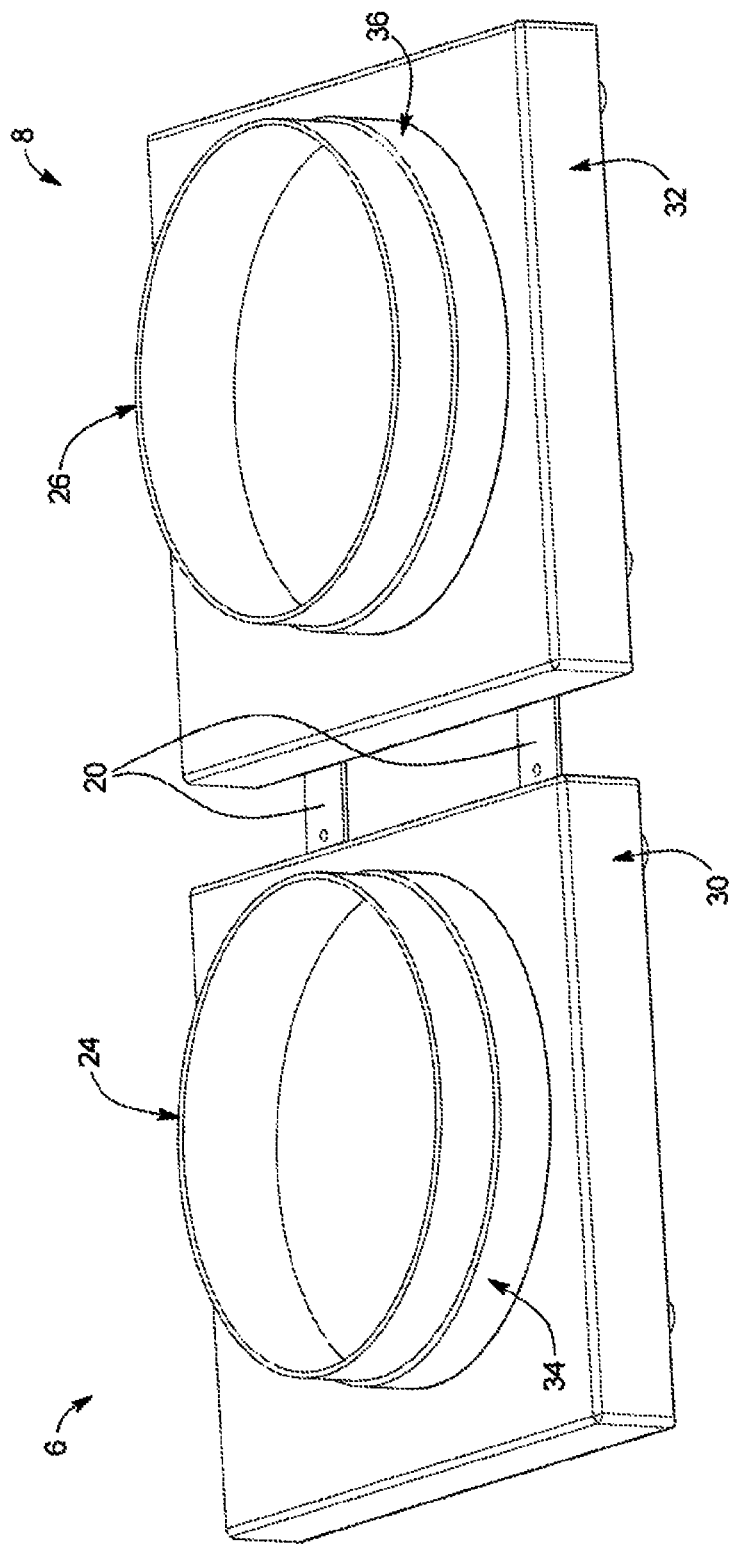
FIG. 2 illustrates two removably attached scales of the remote data collecting system in an embodiment of the invention.
Figure 3:
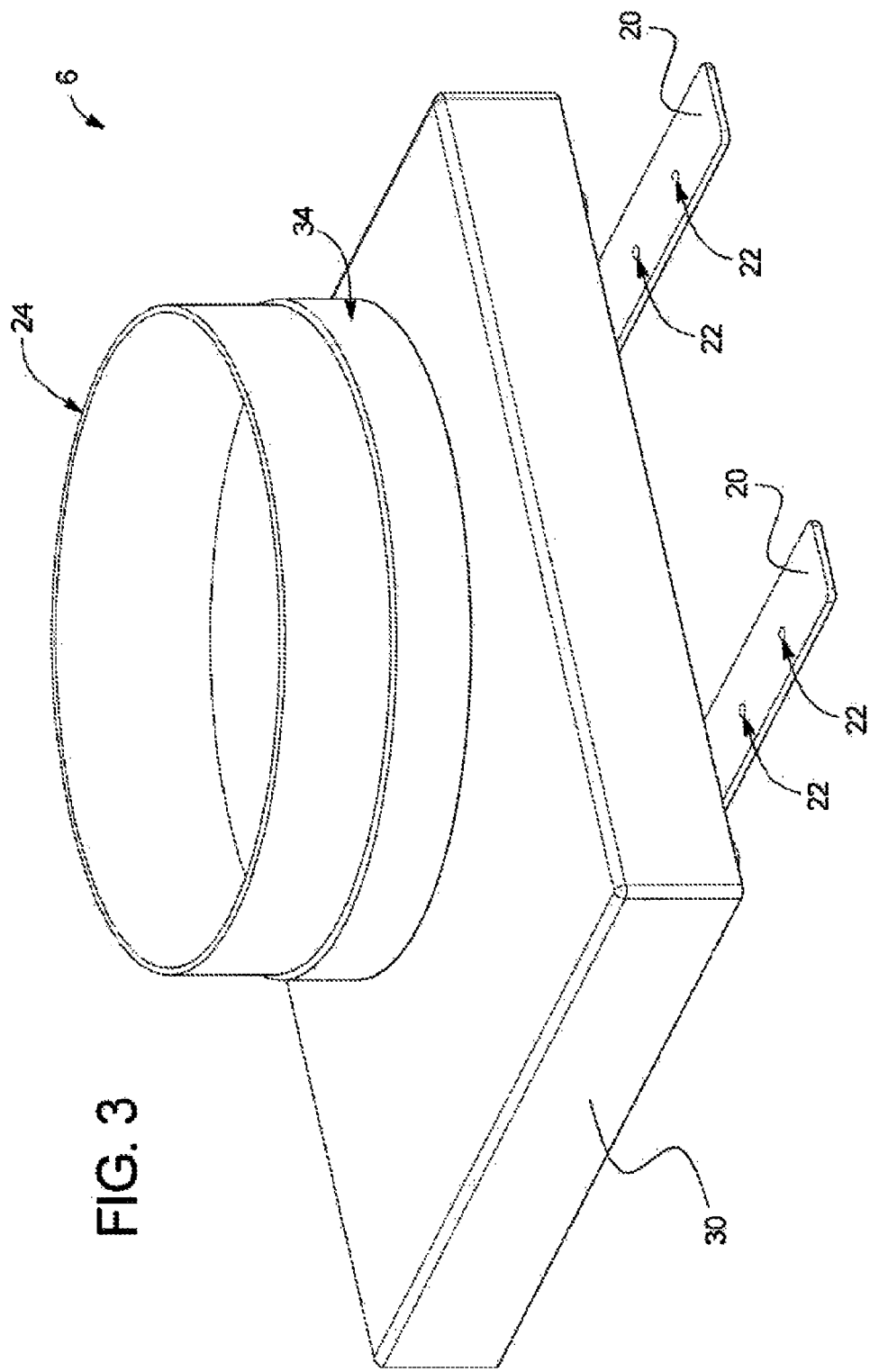
FIG. 3 illustrates a top perspective view of a scale of the remote data collecting system in an embodiment of the invention.
Figure 4:
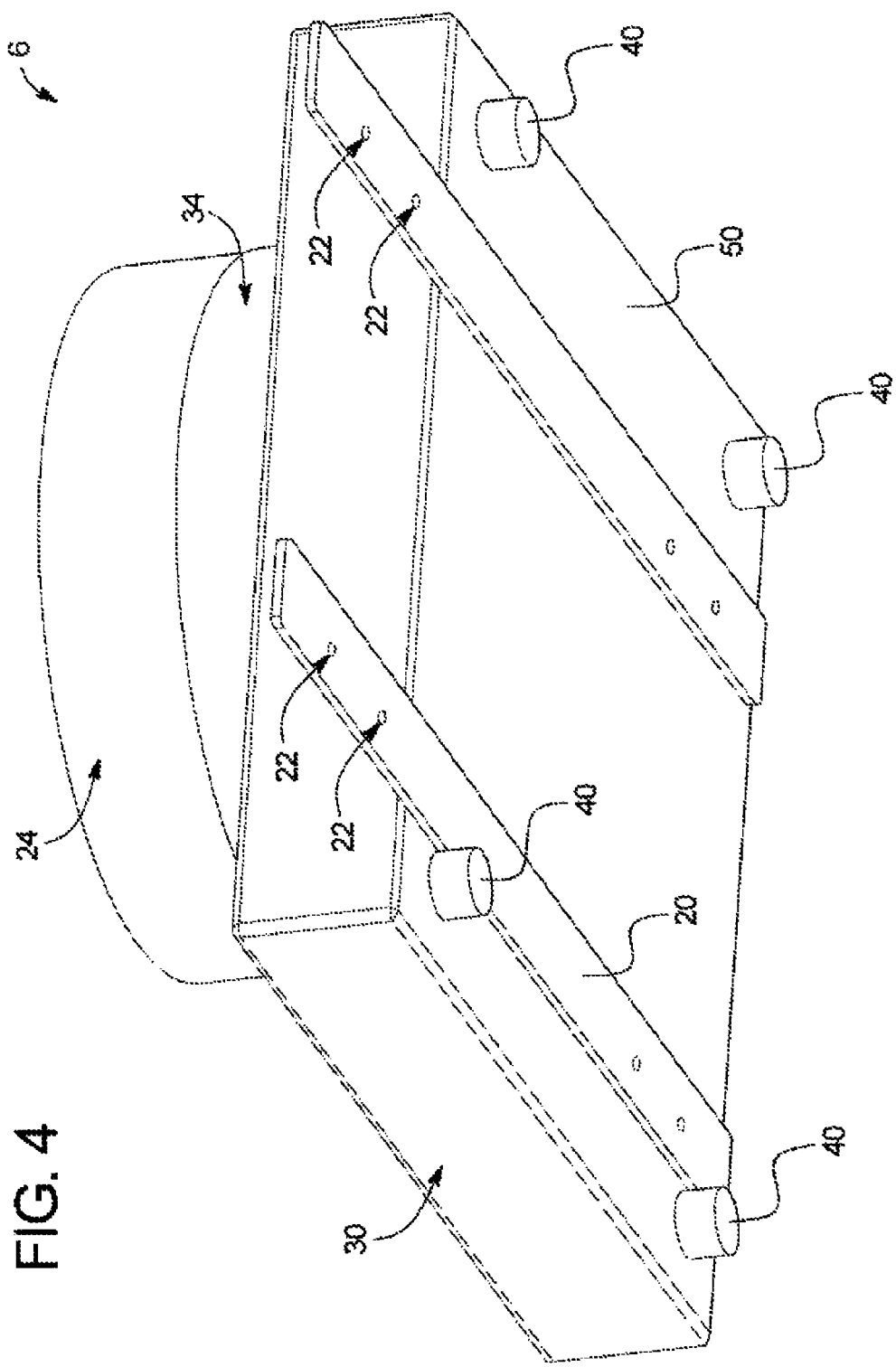
FIG. 4 illustrates a bottom perspective view of the scale of the remote data collecting system in an embodiment of the invention.
Figure 5:
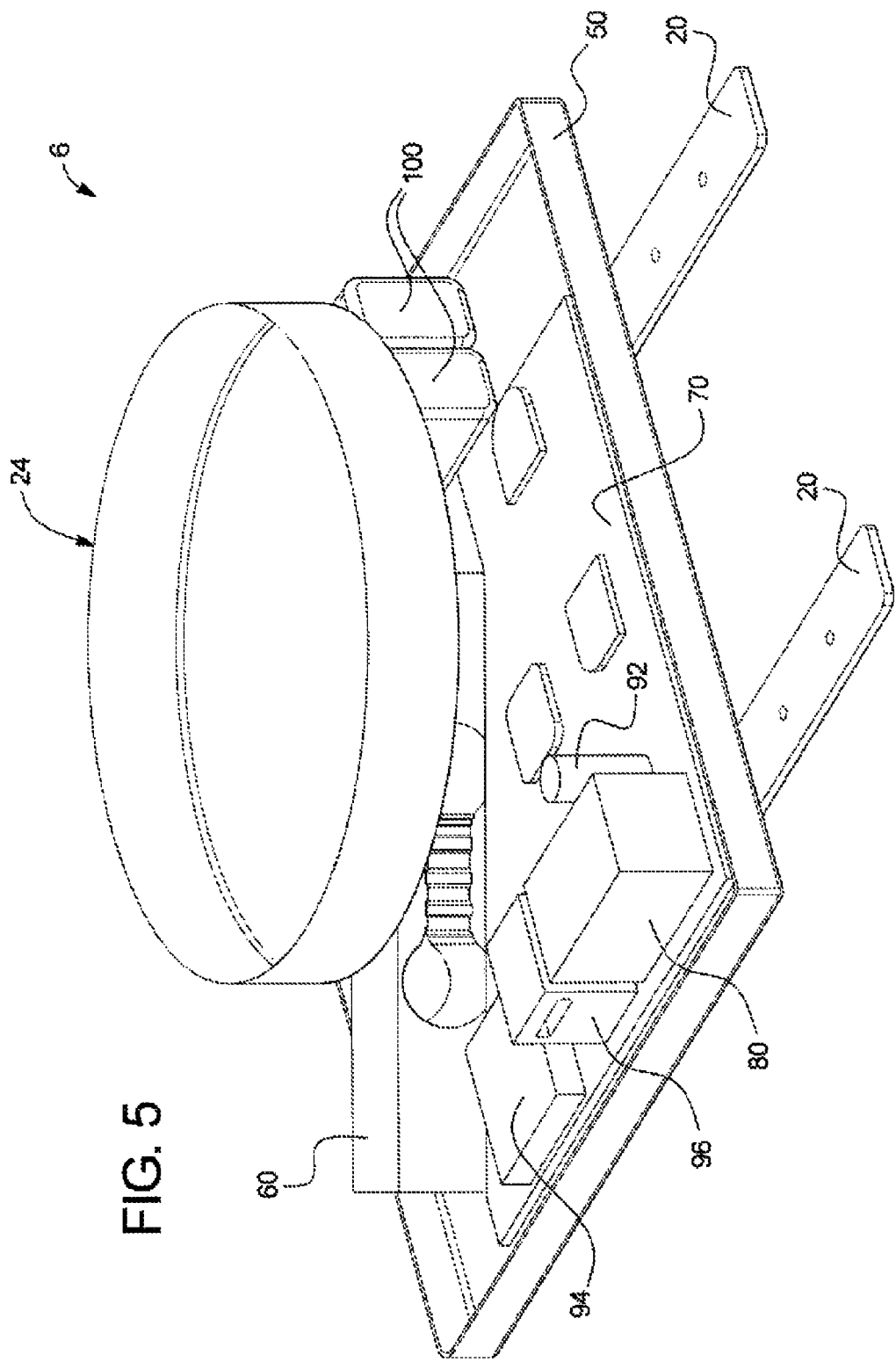
FIG. 5 illustrates a bowl and the internal components of the scale of the remote data collecting system in an embodiment of the invention.

The term "web server" means the hardware (e.g., a computer) and/or the software a computer application) that helps to store, process and deliver content that can be accessed through the internet, for example, via a web page hosted by the web server.

The term "animal" means any animal that could benefit from weight loss and management. The animal can include a human, avian, bovine, canine, equine, feline, hicrine, lupine, murine, ovine, or porcine animal. The animal can also be any suitable pet or companion animal.

The term "companion animal" means a dog or a cat.

The term "single package" means that the components of a kit are physically associated in or with one or more containers and considered a unit for manufacture, distribution, sale, or use. Containers include, but are not limited to bags, boxes, cartons, bottles, packages of any type or design or material, over-wrap, shrink-wrap, affixed components (e.g., stapled, adhered, or the like), or combinations thereof. A single package ma be containers of individual components physically associated such that they are considered a unit for manufacture, distribution, sale, or use.

The term "virtual package" means that the components of a kit are associated by directions on one or more physical or virtual kit components instructing the user how to obtain the other components, e.g., a bag or other container containing one component and directions instructing the user to go to a website, contact a recorded message or a fax-back service, view a visual message, or contact an instructor to obtain instructions on how to use the kit or safety or technical information about one or more components of a kit.

All percentages expressed herein relating to the components of a composition are by weight of the total weight of the composition unless expressed otherwise.

As used throughout, ranges are used herein in shorthand, so as to avoid having to set out at length and describe each and every value within the range. Any appropriate value within the range can be selected, where appropriate, as the upper value, lower value, or the terminus of the range.

As used herein and in the appended claims, the singular form of a word includes the plural, and vice versa, unless the context clearly dictates otherwise. Thus, the references "a", "an", and "the" are generally inclusive of the plurals of the respective terms. For example, reference to "a measuring device" or "a method" includes a plurality of such "measuring devices" or "methods". Similarly, the words "comprise", "comprises", and "comprising" are to be interpreted inclusively rather than exclusively. Likewise, the terms "include", "including" and "or" should all be construed to be inclusive, unless such a construction is clearly prohibited from the context. Where used herein the term "examples," particularly when followed by a listing of terms is merely exemplary and illustrative, and should not be deemed to be exclusive or comprehensive.

The devices, assemblies, kits, methods, compositions and other advances disclosed herein are not limited to particular methodology, protocols and reagents described herein because, as the skilled artisan will appreciate, they may vary. Further, the terminology used herein is for the purpose of describing particular embodiments only and is not intended to, and does not, limit the scope of that which is disclosed or claimed.

The Invention

The present invention is generally directed to remote data collecting systems. For example, the remote data collecting systems can provide real-time information with respect to an amount of product (e.g., human or pet food) consumed/removed at a specified location and comparing the preferences of the consumer for the products. This can be accomplished by recording the weight differences of the product with time. In an embodiment, the remote monitoring of a pet or other animal's eating behavior and food consumption can be performed.

Data from a feeding trial can be processed real-time via the internet through a web server. An authorized operator can get access to raw data, review it and validate the results. Raw data can be modified or removed by authorized operators. Only validated data can be involved in statistical analysis. Because data is uploaded and accessed via the internet, test parameters can be controlled and data accessed from multiple locations by one or more users in real-time. In addition, with internet accessibility, it becomes a network to anyone around the world. Users can easily get connected with remote data collecting systems while accessing a web site.

In one aspect illustrated in FIG. 1, the present invention provides a remote data collecting system 2 comprising a measuring device 4 having a first scale 6 and a second scale 8. Each of scales 6 and 8 can be in communication with a web server 10 via any suitable wired or wireless connection. Scales 6 and 8 include a receptacle (e.g., bowl) for holding a product. Scales 6 and 8 can be removably attached to each other. It should be appreciated that measuring device 4 can comprise more than two scales and operate in a similar manner. Any amount of product removed from each of the plurality of scales can be determined and compared. Moreover, two or more measuring devices can also be in communication with the same web server for use with a plurality of testing sites.

A web site hosted by web server 10 can be built as a platform to store data, monitor remote data collecting system 2, and send commands to remote data collecting system 2. Communication and control of remote data collecting system 2 and analysis of the data can be done from any computing device 12 having internet access worldwide. This allows one or more operators or users with a computing device 12 accessible to the interact to collect, display, distribute, and analyze data from remote data collecting system 2 as well as control remote data collecting system 2 on the web site. This flexibility allows anyone who can access this web site to view the database and operate remote data collecting system 2, especially in real-time.

Computing device 12 is in communication with web server 10. Computing device 12 has the ability to collect and distribute data related to product removed, from the receptacle of each scale. Computing device 12 can be any suitable device allowing access to web server 12 including, for example, a personal computing device, a cell phone, a smart phone, a personal digital assistant, a tablet, a notebook, a laptop, or a combination thereof.

Remote data collecting system 2 can measure food intake data and upload such data to web server 10 for analysis, for example, using as wired connection such as local area network ("LAN") or using a wireless connection such as Wi-Fi connection or General Packet Radio Service ("GPRS") communication.

In a general exemplary embodiment illustrated in FIGS. 2-6, scales 6 and 8 can be removably connected together through one or more connecting sticks 20, which can provide any specified distance between scales 6 and 8. Sticks 20 can define one or more holes 22 to easily allow the distance between scales 6 and 8 to be manually or automatically adjusted.

Scales 6 and 8 can further comprise one or more bowls 24 and 26 placed on top of scales 6 and 8. Bowls 24 and 26 can be removably or permanently attached to scales 6 and 8, respectively, in an embodiment, bowls 24 and 26 can be placed and fixed to scales 6 and 8 through a magnet system, which prevents bowls 24 and 26 from being moved from scales 6 and 8 by the consumer or pet.

Each of scales 6 and 8 can comprise a scale top cover 30 and 32 made of any suitable material such as, for example, stainless steel. The material can be specified for any hygienic requirements. Each of covers 30 and 32 can comprise a bowl holder 34 and 36, which can be used to position bowls 24 and 26 directly over weight sensors in scales 6 and 8 underneath to bowls 24 and 26. Scales 6 and 8 can further comprise feet 40 to keep scales 6 and 8 stationery on any type of floor.

Scales 6 and 8 further include an electronic scale 60, a circuit board 70, a data memory device 80, and a data transmission system 90. Scales 6 and 8 can also include a GPRS system 92, a Wi-Fi module 94, and/or cable connection port 96. Electronic components that support Wi-Fi connections can also provide cable connection functions. Each of the components of scales 6 and 8 are in communication with each other.

Scales 6 and 8 can further include a battery power pack 100 so as to be portable. It should be appreciated that the scales can also be designed to be connected to a wall outlet or other external power source in addition to or in place of the battery power pack 100. In an embodiment, the main power or external supply can be used as first priority then followed by a rechargeable battery and/or regular battery.

It should be appreciated that scales 6 and 8 do not need to comprise every single one of these components. In alternative embodiments, the scales can comprise any one or more of the previously described components according to the objectives of remote data collecting system 2.

During use, data memory device 80 records on scales 6 and 8 weight changes of pet food and records the weighing date and time. Data is stored in data memory device 80 until it is replaced by new data recorded by scales 6 and 8.

Data transmission system 90 functions via connection to web server 10 and data transfers from the data memory device 80 to a specific website hosted by we server 10. Data transmission system 90 is also able to get operation commands from the website and send statuses back about measuring device 4. Data transmission system 90 is able to transfer data via a Wi-Fi module 94, GPRS system 92 and/or internet cable connection 96. In an embodiment, data transmission system 90 will automatically test which communication method is available. If the preferred method is not available at the moment, data transmission system 90 can switch to another communication method. Once the connection is done, the communication can start and continue until measuring device 4 is switched off. Data transmission system 90 can connect to web server 10 frequently, for example, up to every 30 seconds (or more or less) so as to be considered a real-time communication.

Scales 6 and 8 can measure food consumption by weighing the food amounts and calculating the changes. Such data can be collected real-time during any suitable desirable intervals. For example, the data can be collected every second or every minute for a predetermined amount of time. Remote data collecting system 2 can connect with web server 10 and upload data that it recorded in real-time. The data from remote data collecting system 2 can then be statistically analyzed on a website hosted by web server 10 to determine palatability and/or feed consumption related information. The website can be accessed and controlled by a computing device 12 used by one or more consumers/testers/operators.

Any weight change recorded by scales 6 and 8 can be stored as data in data memory device 80 and any data stored can be uploaded to a website with access to web server 10 via the Internet. In a working embodiment, a test start time and end time will be sent out from the website via the Internet and stored in each measuring device 4. Data accumulated between test start time and test end time may be differentiated from data accumulated during a time out of preset test duration. It is beneficial for data analyzing in such a way that data with different codes can be classified as useful data or useless data. Only useful data can be automatically taken for data statistical analysis on the website. However, useless data can be taken for data analysis manually. Once remote data collecting system 2 works to end time, it can switch off automatically or be turned off manually.

On the website, information about the animal(s), testing samples, and tests can be setup, recorded and managed. For example, the animal's preset sampling time and validation status, test schedule, and test duration can be saved on the website. On the website, measuring device 4 can be linked to an animal. In this system, there may be multiple animals in multiple locations (e.g., homes of the pets). The website can send commands to each measuring device 4 and deliver test related information. Once measuring device 4 receives or stores preset sampling times and test durations, it can initiate a test and keep working for the duration of the preset sampling time. Measuring device 4 can subsequently shut off automatically when it is not testing.

In another embodiment of an operation, on the website, a specific animal can be selected and its consumption data can be viewed. If a feeding trial with a group of animals at their individual home locations is completed in the same day, data can be analyzed statistically the website. A data analysis screen shows the left and right bowls average weight consumption. The statistical data results for the product first consumed by the animal and product preference by group is shown by p-values. The p-value provides information if the tested product is significantly different from the reference product.

On the website, data transmitted from remote data collecting system 2 can be stored as raw data. Before statistical analysis, a data validation can be taken on the website. An authorized operator can get access to the raw data, review them, and validate the results. Raw data can be modified or removed by authorized operators. Only validated data may be involved in statistical analysis.

Software in measuring device 4 can include an operation monitoring program. Any operational activity and change in working status can be recorded and delivered to the website with access to the Internet. For example, operation information such as switch on operation, test initiation, and status of low battery can be recorded and uploaded to the website. The website can also detect the connection status of measuring device 4. The website can classify and identify the reason of an abnormal status of a scale and a communication status based on information that is uploaded by measuring device 4 and connection status detected by the website. A green, yellow, grey or red light can be shown automatically on the website, representing different working and communication statuses of the scales.

Computing device 12 can include appropriate software for organizing, analyzing and displaying the data. Computing device 12 can be used to initiate testing periods and record testing data in real-time or periodically in desirable intervals. Thus, not only is the consumption of food measured, the rate of consumption can be measured. The remote data collecting system can be designed to avoid false positives, for example, or more of the scales are stepped upon.

Any suitable computing device such as a person computing device, a cell phone, a smart phone, a personal digital assistant, a tablet, a notebook, or a laptop can be sold as part of the remote data collecting system to pet owners, who can monitor his/her pet food consumption from anywhere if the pet owners concern about their pet at home. Computing device 12 can be set up so that the pet owners can send a command or request to remote data collecting system 2. In addition, when one of the scales is not working, data transmission system 90 can send a short message to computing device 12 to remind the pet owner to check the scale or to turn the scale on. Computing device 12 can also include video and picture capture capabilities so that the pet owner can communicate with their pet.

In another aspect, the present invention provides a method of collecting data remotely. This method comprises providing a measuring device having at least two scales in communication with a web server and a computing device in communication with the web server. Each of the scales comprises one or more products. Data can be collected real-time about the amount of product removed from each of the scales and sent to the web server. A data transmission system in the measuring device collects and distributes the data to the web server. Two or more users can access the data from the web server at the same time, for example, via a website hosted by the web server.

In yet another aspect, the invention provides a method of testing the palatability of pet mod remotely and in real-time. The method comprises providing a remote data collecting system comprising a measuring device having at least two scales in communication with a web server and a computing device in communication with the web server. Each of the scales comprises a different pet food. The method further comprises introducing a pet to the pet foods on the scales and collecting data in real-time with respect to the amount of pet food eaten by the pet from each of the scales.

In another aspect, the present invention provides a method of testing the palatability of pet food in real-time in a domestic environment. As used herein, the term "domestic environment" means a location such as a consumer's house, a store, a vehicle, etc., where product research or testing is not typically performed. This method comprises providing a measuring device having at least two scales in communication with is web server and a computing device in communication with the web server. The measuring device is located at the domestic environment. Each of the scales comprises a different pet food. A pet is introduced to the pet foods on the measuring device at the domestic location. Data is collected real-time with respect to the amount of pet food eaten by the pet from each of the scales at the domestic environment.

In any of the methods described herein, any suitable data can be collected and/or recorded from the measuring device. The data can comprise date of trial and amount of food eaten from each scale (e.g., amount eaten, beginning and ending eating time). The data analysis can include the total food consumption for each specific pet and the average amount eaten over time.

The web server can collect and distribute the data to any suitable computing device. The computing device and software system can analyze and display the data using any suitable analysis methods or procedures, for example, via a website. The data can be outputted in a spreadsheet or note pad format. The data can be displayed in the form of a graph, for example, comparing the amount of product removed from each of the scales over a predetermined amount of time.

In an aspect, the present invention provides a kit comprising in separate containers in a single package or in separate containers in a virtual package, as appropriate for the kit component, either (A) a remote data collecting system comprising a measuring device having at least two scales in communication with a web server and a computing device in communication with the web server, or (B) a measuring device having at least two scales, and at least one of (1) a web server, (2) a computing device, (3) instructions on how to use the measuring device for determining the palatability of a food product, (4) instructions on how to use the measuring device at a remote location, (5) instructions on how to use the computing device to analyze data collected from the measuring device, (6) one or more bowls to be used in conjunction with the scales, or (7) one or more pet foods to be used in conjunction with the measuring device.

When the kits comprise a virtual package, the kits are limited to instructions in a virtual environment in combination with one or more physical kit components. The kits may contain the kit components in any of various combinations. In one embodiment, the kit contains a measuring device as described herein. In another embodiment, one or more computing devices, food products, or instructions can be sold with this kit or sold separately from the kit, for example, as part of a virtual kit.

The kits can encompass one or more kit components that are ordered and shipped separately to a consumer, for example, such as an order on the internet or by phone for a measuring device and a computing device, wherein the two articles are shipped from separate locations to the consumer's address.

In a further aspect, the present invention provides a means for communicating information about or instructions for one or more of (1) using a remote data collecting system comprising a measuring device having at least two scales in communication with a web server and a computing device in communication with the web server, (2) using the remote data collecting system to determine consumer preferences for a food product, (3) using the remote data collecting system to determine palatability of a human or nonhuman food product, preferably a pet food, most preferably a dog or cat pet food, or (4) nutritional information regarding the human or non-human food product.

The communication means can be a document, digital storage media, optical storage media, audio presentation, or visual display containing the information or instructions. In certain embodiments, the communication means can be a displayed website, a visual display kiosk, a brochure, a product label, a package insert, an advertisement, a handout, a public announcement, an audiotape, a videotape, digital streaming, a DVD, a CD-ROM, a computing device readable chip, a computing device readable card, a computing device readable disk, a USB device, a FireWire device, a computing device memory, and any combination thereof containing such information or instructions.

Additional useful information includes one or more of (1) methods and techniques for setting-up, using, and monitoring the system, particularly methods for placing product on the system scales, and (2) contact information for animals or their caregivers to use if they have a question about the system and its use. Useful instructions include methods for loading food onto the scales of the system. The communication means is useful for instructing on the benefits of using the system.

In another aspect, the invention provides a package including indicia describing a remote data collecting system comprising a measuring device having at least two scales in communication with a web server. The indicia can be in the form of words, symbols, pictures, photographs, figures, or combinations thereof to show details or examples of the remote data collecting system described herein. The package can further contain a remote data collecting system comprising a measuring device having at least two scales in communication with a web server. In addition, the package may contain a computing device to be used in conjunction with the measuring device.

In an embodiment, the package can include one or more handles suitable for handling and transporting the package. The package can include one or more windows for viewing the measuring device or any parts thereof. The package can include a label affixed to the package containing a word or words, picture, design, acronym, slogan, phrase, or combination thereof, that indicates that the package contains a remote data collecting system comprising a measuring device having at least two scales in communication with a web server.

EXAMPLES

The invention can be further illustrated by the following example, although it will be understood that this example is included merely for purposes of illustration and is not intended to limit the scope of the invention unless otherwise specifically indicated.

Example 1

Dry Cat Food from a single one batch of product was repacked in laminated aluminum pouches and labeled as X and Y products for left side bowl and right side bowl, respectively. Food samples X and Y were distributed to each of 38 cat owners in the network. A test to determine a preference between the two products was carried out as follows.

The system was activated and pre-test validation done as described in Example 1.

Place two balances on floor side by side.

Each owner switched on the devices and emptied the pouch of product X in the bowl of one electronic balance on left hand side and product Y into the bowl of the other balance on right.

The bowls were then placed on the respective balances.

The cat was then left alone to eat from either bowl.

A summary of test product set up is shown in Tables 1 and 2.

As the cat consumed the food and weight on the balances changed, it was recorded and transmitted to the website (http://pesdog.gengyan.com) for determination of initial choice (the side of food bowl that pet first consumed food in it); preference the side of food bowl that pet consumed more food in it than consumed food in the other bowl); and total consumption after 10 hours.

The raw data collected are analyzed statistically and data for initial choice, preference, and total consumption preference and shown in Table 3.

The result indicates that no difference in preference was seen between product X and product Y. This was not unexpected because it was the same food in each bowl but it did also confirm that there was no significant left or right bowl bias.

TABLE 1

| Reference | Position | Batch ID for Test | Type | Production Date |
|---|---|---|---|---|
| X | Left | 165753 | Dry - Food | Jan. 09, 2011 |
| Y | Right | 165752 | Dry - Food | Jan. 09, 2011 |

TABLE 2

| Number of Cat Assigned | Number of Cats - Valid Data | Number of Cats Excluded - Invalid Data |
|---|---|---|
| 38 | 31 | 5 |

TABLE 3

| | X | Y | Significance at $p \leq 0.05$ |
|---|---|---|---|
| Initial Choice (%) | 54.5 | 45.5 | 0.6 |
| Preference (%) | 48.5 | 48.5 | 1.0 |
| Average % Consumption | 50.8 | 49.2 | 0.865 |

In the specification, there have been disclosed typical preferred embodiments of the invention and, although specific, terms are employed, they are used in a generic and descriptive sense only and not for purposes of limitation, the scope of the invention being set forth in the claims. Obviously many modifications and variations of the invention are possible in light of the above teachings. It is therefore to be understood that within the scope of the appended claims the invention may be practiced otherwise than as specifically described.

What is claimed is:

1. A method of collecting data remotely comprising:
providing a remote data collecting system comprising a measuring device having at least two scales, each of the scales in communication with a web server and a computing device in communication with the web server, each of the scales comprising a weight sensor and a pet food, the web server hosting a website accessed and controlled by the computing device over the internet;
accepting preset sampling times and a test duration on the website from the computing device;
sending a start time, an end time and the preset sampling times from the website to the measuring device;
collecting data with respect to the amount of the pet food removed from each of the scales from the start time to the end time; and
displaying the data on the computing device using the website.

2. The method of claim 1 wherein each of the scales includes a data memory device and a data transmission system.

3. The method of claim 2 wherein the data transmission system collects and distributes the data to the web server.

4. The method of claim 2 wherein two or more users can access the data from the web server at the same time using the website.

5. The method of claim 1 wherein the measuring device is one of a plurality of measuring devices, the website sends commands to each of the plurality of measuring devices, and the website associates each of a plurality of animals at a plurality of testing sites with a corresponding measuring device of the plurality of measuring devices.

6. The method of claim 5 comprising receiving a selection of a specific animal of the plurality of animals, the website receives the selection from the computing device, and the website displays consumption data on the computing device for the specific animal identified by the selection.

7. The method of claim 1 wherein the measuring device shuts off automatically after a predetermined period when not in use.

8. The method of claim 1 wherein the web server conducts a plurality of trials for determining amounts of the pet food removed from each of the scales.

9. The method of claim 1 wherein the data is transferred from the measuring device to the web server via at least one of a Wi-Fi connection, a general pack radio service communication, an internet cable connection, or a local area network.

10. A method of testing the palatability of pet food remotely and in real-time, the method comprising:
providing a remote data collecting system comprising a measuring device having at least two scales, each of the scales in communication with a web server and a computing device in communication with the web server, each of the scales comprising a weight sensor and a different pet food, the web server hosting a website accessed and controlled by the computing device over the internet;

accepting preset sampling times and a test duration on the website from the computing device;

sending a start time, an end time and the preset sampling times from the website to the measuring device;

introducing a pet to the pet foods on the scales;

collecting data in real-time with respect to the amount of pet food eaten by the pet from each of the scales from the start time to the end time; and displaying the data on the computing device using the website.

11. A method of testing the palatability of pet food in real-time in a domestic environment comprising:

providing a remote data collecting system comprising a measuring device having at least two scales, each of the scales in communication with a web server and a computing device in communication with the web server, the measuring device being located at the domestic environment, each of the scales comprising a weight sensor and a different pet food, the web server hosting a website accessed and controlled by the computing device over the internet;

accepting preset sampling times and a test duration on the website from the computing device;

sending a start time, an end time and the preset sampling times from the website to the measuring device;

introducing a pet to the pet foods on the measuring device;

collecting data in real-time with respect to the amount of pet food eaten by the pet from each of the scales at the domestic environment from the start time to the end time; and displaying the data on the computing device using the website.

12. The method of claim 11 wherein the domestic environment is selected from the group consisting of a house, a store, a vehicle and combinations thereof.

13. The method of claim 1 wherein an authorized operator accesses, reviews and validates raw data through the website, and validating the raw data comprises modifying or removing a portion of the raw data such that a remainder of the raw data is validated data, and the website performs statistical analysis using only the validated data.

14. The method of claim 3 wherein the data transmission system connects to the web server at least once every thirty seconds.

15. The method of claim 11 wherein each of the scales includes a data memory device and a data transmission system.

16. The method of claim 15 wherein the data memory device records weight changes of the pet food on the corresponding scale in association with dates and times.

17. The method of claim 11 wherein each of the scales comprises a component selected from the group consisting a battery power pack, a rechargeable or regular battery, a circuit board, and combinations thereof.

18. The method of claim 11 wherein the scales are removably attached to each other.

19. The method of claim 11 wherein the computing device is selected from the group consisting of a personal computing device, a cell phone, a smart phone, as personal digital assistant, a tablet, a notebook, a laptop, and combinations thereof.

20. The method of claim 11 wherein each of the scales comprises a cover comprising a bowl holder that receives a bowl that contains the pet food, and the bowl holder of each of the scales positions the corresponding bowl on the corresponding weight sensor.

* * * * *

UNITED STATES PATENT AND TRADEMARK OFFICE
CERTIFICATE OF CORRECTION

PATENT NO. : 9,693,573 B2
APPLICATION NO. : 13/785896
DATED : July 4, 2017
INVENTOR(S) : Xue Ling Wang et al.

It is certified that error appears in the above-identified patent and that said Letters Patent is hereby corrected as shown below:

At Column 2, Line 53, please change "ma" to -- may --.

At Column 4, Line 8, please change "interact" to -- Internet --.

At Column 5, Line 10, please change "we" to -- web --.

At Column 7, Line 2, please change "mod" to -- food --.

Signed and Sealed this
First Day of May, 2018

Andrei Iancu
*Director of the United States Patent and Trademark Office*